US007671036B2

(12) United States Patent
Katzhendler et al.

(10) Patent No.: US 7,671,036 B2
(45) Date of Patent: Mar. 2, 2010

(54) POSITIVELY-CHARGED PEPTIDE NUCLEIC ACID ANALOGS WITH IMPROVED PROPERTIES

(75) Inventors: Jehoshua Katzhendler, Jerusalem (IL); Ada Schlossman, Jerusalem (IL); Yousuf Najajreh, Bethlehem (IL); Dan Gibson, Jerusalem (IL)

(73) Assignee: Yissum Research Development Company of The Hebrew University of Jerusalem, Jerusalem (IL)

( * ) Notice: Subject to any disclaimer, the term of this patent is extended or adjusted under 35 U.S.C. 154(b) by 579 days.

(21) Appl. No.: 10/297,788

(22) PCT Filed: Jun. 22, 2001

(86) PCT No.: PCT/IL01/00570

§ 371 (c)(1), (2), (4) Date: Jun. 2, 2003

(87) PCT Pub. No.: WO01/98522

PCT Pub. Date: Dec. 27, 2001

(65) Prior Publication Data

US 2004/0034043 A1    Feb. 19, 2004

(51) Int. Cl.
*A01N 43/04* (2006.01)
*A61K 31/70* (2006.01)
*A01N 43/90* (2006.01)
*C07D 473/00* (2006.01)

(52) U.S. Cl. ............... 514/44; 514/263.4; 544/276; 544/277

(58) Field of Classification Search ............... None
See application file for complete search history.

(56) References Cited

U.S. PATENT DOCUMENTS 6,506,594 B1 * 1/2003 Barany et al. ............ 435/287.2
6,660,845 B1 * 12/2003 Gall et al. ................. 536/23.1

FOREIGN PATENT DOCUMENTS

| EP | 0646595 | | 4/1995 |
|---|---|---|---|
| WO | WO 9504749 A | | 2/1995 |
| WO | WO 9504749 A1 | * | 2/1995 |
| WO | WO 9602558 A1 | * | 2/1996 |

OTHER PUBLICATIONS

Rasmussen et al. Evaluation of Transfection Protocols for Unmodified and Modified Peptide Nucleic Acid (PNA) Oligomers. (2006). Oligonucleotides, vol. 16, pp. 43-57.*
Hyrup et al. Bioorganic & Medicinal Chemistry Letters, vol. 6, Issue 10, May 21, 1996, pp. 1083-1088. (See IDS).*
Uhlmann et al. Angew. Chem. Int. Ed. 1998, vol. 37, 2796-2823. (See IDS).*

G Lowe, T Vilaivan—Journal of the Chemical Society, Perkin Transactions vol. 1, 1997, pp. 539-546. Title: Amino acids bearing nucleobases for the synthesis of novel peptide nucleic acids. -IDS-Aug. 15, 2005.*
Kuwahara et al. 1999, Nucleic Acids Symposium Series No. 42 31-32.*
Hyrup, et al., *A Flexible and Positively Charged PNA Analogu With An Ethylene-Linker To The Nucleobase: Synthesis an Hybridization Properties*, Bioorganic & Medical Chemistr Letters, 6:10 pp. 1083-1088 (1996) (Exhibit 3).
Uhlmann et al., *PNA: Synthetic Polyamide Nucleic Acids with Unusual Binding Properties, Angew. Chem. Int. Ed.*, 37:2796-2823 (1998) (Exhibit 4).
International Search Report issued Mar. 14, 2002 (Exhibit 5).
International Preliminary Examination Report issued Nov. 12, 2004 (Exhibit 6).
Agrawal S. et al., Phosphoramidate, Phosphorothioate, And Methylphosphonate Analogs Of Oligodeoxynucleotide: Inhibitors Of Replication Of Human Immunodeficiency Virus, *Nucleosides & Nucleotides* (1989) vol. 8, pp. 819-823.
Agrawal S., Antisense Oligonucleotides: A Possible Approach For Chemotherapy Of AIDS, Prospects for Antisense Nucleic Acid *Therapy of Cancer and AIDS* (1991) pp. 143-158.
Batteur S.P. et al., Antisense Oligodeoxynucleotide To Inducible Nitric Oxide Synthase Protects Against Transient Focal Cerebral Ischemia-Induced Brain Injury, *Journal Of Cerebral Blood Flow and Metabolism* (2001) vol. 21, pp. 15-21.
Bickel U., Antibody Delivery Through The Blood-Brain Barrier, *Advanced Drug Delivery Reviews* (1995) vol. 15, pp. 53-72.
Bickel U. et al., Delivery Of Peptides And Proteins Through The Blood-Brain Barrier, *Advanced Drug Delivery Reviews* (2001) vol. 46, pp. 247-279.
Boado R. J. and Pardridge W.M., Complete Inactivation Of Target Mrna By Biotinylated Antisense Oligodeoxynucleotide-Avidin Conjugates, *Bioconjugate Chem.* (1994) vol. 5, pp. 406-410.
Boado R. J., Antisense Drug Delivery Through The Blood-Brain Barrier, *Advanced Drug Delivery Reviews* (1995) vol. 15, pp. 73-107.
Brightman M.W., Morphology Of Blood-Brain Interfaces, *Exp. Eye Res.* (1977) pp. 1-25.
Duda J.E. et al., Neuropathology Of Synuclein Aggregates: New Insights Into Mechanisms Of Neurodegenerative Diseases, *Journal of Neuroscience Research* (2000) vol. 61, pp. 121-127.
Greig, Nigel H., Drug Delivery To The Brain By Blood-Brain Barrier Circumvention and Drug Modification, *In Implications of the Blood-Brain Barrier and its manipulation* (1989) vol. 1, (Neuwelt, E.A., ed.), pp. 311-367, Plenum Press, New York, USA.
Haller H. et al., Antisense Oligonucleotides For Icam-1 Attenuate Reperfusion Injury And Renal Failure In The Rat, *Kidney International* (1996) vol. 50, pp. 473-480.
Huber, Andrea B. and Martin E. Schwab, Nogo-A Potent Inhibitor of Neurite Outgrowth and Regeneration, *Biol. Chem.* (2000), vol. 381, Nos. 5-6, pp. 407-419.

(Continued)

*Primary Examiner*—Janet L. Epps-Smith
(74) *Attorney, Agent, or Firm*—John P. White; Cooper & Dunham LLP (57) ABSTRACT

The present invention relates to novel types of peptide nucleic acids (PNAS) with improved properties. In particular, it relates to positively charged PNA units having an ethylene linker between the backbone and the nucleobase, to oligonucleotide analogs comprising these units, to oligomers comprising these units, and to the use of positively charged PNAs as novel delivery agents with therapeutic and diagnostic applications including for antisense therapy.

24 Claims, 1 Drawing Sheet

OTHER PUBLICATIONS

Kiely, John S., Recent Advances in Antisense Technology, *Annual Reports In Medicinal Chemistry* (1994) Ch. 39, vol. 29, pp. 297-306.

Kuwahara M. et al., Synthesis Of Δ-Amino Acids With An Ether Linkage In The Main Chain And Nucleobases On The Side Chain As Monomer Units For Oxy-Peptide Nucleic Acids, *Tetrahedron* (1999) vol. 55, pp. 10067-10078.

Lagriffoule P. et al., Peptide Nucleic Acids With A Conformationally Constrained Chiral Cycloheyxl-Derived Backbone, *Chem. Eur. J.* (1997) vol. 3, No. 6, pp. 912-919.

Li Y. MD at al., P53-Immunoreactive Protein And P53 MRNA Expression After Transient Middle Cerebrak Artery Occlusion In Rats, *Stroke* (1994) vol. 25, No. 4, pp. 849-856.

Loschener T. and Joachim W. Engels, Methylphosphonamidites: Preparation And Application In Oligodeoxynucleoside Methylphosphonate Synthesis, *Nucleosides & Nucleotides* (1988) vol. 7, Nos. 5&6, pp. 729-732.

Lowe G. and Vilaivan T., Amino Acids Bearing Nucleobases For The Synthesis Of Novel Peptide Nucleic Acids, *J. Chem. Soc., Perkin Trans.* (1997) vol. 1, pp. 539-546.

Lowe G. and Vilaivan T., Dipeptides Bearing Nucleobases For The Synthesis Of Novel Peptide Nucleic Acids, *J. Chem. Soc., Perkin Trans.* (1997) vol. 1, pp. 547-554.

Lowe G. and Vilaivan T., Solid-Phase Synthesis Of Novel Peptide Nucleic Acids, *J. Chem. Soc., Perkin Trans.* (1997) vol. 1, pp. 555-560.

Mayne, M., Ph.D. et al., Antisense Oligodeoxy Nucleotide Inhibition of Tumor Necrosis Factor-α Expression Is Neuroprotective After Intercebral Hemorrhage, *Stroke* (2001) vol. 32, pp. 240-248.

Oldendorf W.H., Lipid Solubility And Drug Penetration Of The Blood Brain Barrier, *Proceedings Of The Society For Experimental Biology And Medicine* (1974) vol. 147, pp. 813-816.

Pardridge W.M. et al., Vector-Mediated Delivery Of A Polyamide ("Peptide") Nucleic Acid Analogue Through The Blood-Brain Barrier In Vivo, *Proc. Natl. Acad. Sci. USA* (1995) vol. 92, pp. 5592-5596.

Pooga M. et al., PNA Oligomers As Tools For Specific Modulation Of Gene Expression, *Biomolecular Engineering* (2001) vol. 17, pp. 183-192.

Ruben D.W. and Pardridge W.M., Pharmacokinetics And Blood-Brain Barrier Transport Of 3H-Biotinylated Phosphorothioate Oligodeoxynucleotide Conjugated To A Vector-Mediated Drug Delivery System1, *The Journal of Pharmacology and Experimental Therapeutics* (1996) vol. 276, No. 1, pp. 206-212.

Schwarze S.R. et al., In Vivo Protein Transduction: Delivery Of A Biologically Active Protein Into The Mouse, *Science* (1999) vol. 285, pp. 1569-1572.

Shohami E. et al., Antisense Prevention Of Neuronal Damages Following Head Injury In Mice, *Journal of Molecular Medicine* (2000), pp. 228-243.

Simantov R. et al., Dopamine-Induced Apoptosis In Human Neuronal Cells: Inhibition By Nucleic Acids Antisense To The Dopamine Transporter, *Neuroscience* (1996) vol. 74, No. 1, pp. 39-50.

Stein C.A. and Cohen J.S., Oligodeoxynucleotides As Inhibitors Of Gene Expression: A Review, *Cancer Research* (1988) vol. 48, pp. 2659-2668.

Tamai I. and Tsuji A., Transporter-Mediated Permeation Of Drugs Across The Blood-Brain Barrier, *Journal of Phamaceutical Sciences* (2000) vol. 89, No. 11, pp. 1371-1388.

Temsamani J. et al., Brain Drug Delivery Technologies: Novel Approaches For Transporting Therapeutics, *PSTT* (2000) vol. 3, No. 5, pp. 155-162.

Tsuji A. and Tamai I., Carrier-Mediated Or Specialized Transport Of Drugs Across The Blood-Brain Barrier, *Advanced Drug Delivery Reviews* (1999) vol. 36, pp. 277-290.

Vassar R. et al., β-Secretase Cleavage Of Alzheimer's Amyloid Precursor Protein By The Transmembrane Aspartic Protease BACE, *Science* (1999) vol. 286, pp. 735-741.

Wahlestedt C. et al., Antisense Oligodeoxynucleotides To NMDA-R1 Receptor Channel Protect Cortical Neurons From Excitotoxicity And Reduce Focal Ischaemic Ifarctions, *Nature* (1993) vol. 363, pp. 260-263.

Wattiaux R. et al., Endosomes, Lysosomes: Their Implication In Gene Transfer, *Advanced Drug Delivery Reviews* (2000) vol. 41, pp. 201-208.

Weinfeld M. and Livingston D.C., Synthesis And Properties Of Oligodeoxyribonucleotides Containing An Ethylated Internucleotide Phosphate, *Biochemistry* (1986) vol. 25, pp. 5083-5091.

Whitesell L. et al., Stability, Clearance, And Disposition Of Intraventricularly Administrered Oligodeoxynucleotides: Implications For Therapeutic Application Within The Central Nervous System, *Proc. Natl. Acad. Sci. USA* (193) vol. 90, pp. 4665-4669.

Wu, Defang et al., Pharmacokinetics and Blood-Brain Barrier Transport of [$^3$H]-Biotinylated Phosphorothioate Oligodeoxynucleotide Conjugated To A Vector-Mediated Drug Delivery System, *The Journal of Pharmacology and Experimental Therapeutics* (1996) vol. 276, No. 1, pp. 206-211; and.

Yang G.Y. et al., Inhibition Of TnFα Attenuates Infarct Volume And ICAM-1 Expression In Ischemic Mouse Brain, *Neuro Report* (1998) vol. 9, pp. 2131-2134.

* cited by examiner

Figure 1

Modified PNA                                  PNA

POSITIVELY-CHARGED PEPTIDE NUCLEIC ACID ANALOGS WITH IMPROVED PROPERTIES

FIELD OF THE INVENTION

The present invention relates to novel types of peptide nucleic acids (PNAs) with improved properties. In particular it relates to positively charged PNA units having an ethylene linker between the backbone and the nucleobase, to oligonucleotide analogs containing these units, to oligomers comprising these units, and to the use of positively charged PNAs as novel delivery agents with therapeutic and diagnostic applications including for antisense therapy.

BACKGROUND OF THE INVENTION

Synthetic antisense oligonucleotides have been used to inhibit DNA replication and protein synthesis with very high specificity[1,2]. Various inhibition mechanisms have been proposed including:

1. Prevention of ribosomal complex assembly or mRNA translation (by hybridization of the antisense oligonucleotide to its target RNA molecule).

2. Degradation of the resultant DNA/RNA duplex by RNaseH.

3. Inhibition of the pre-mRNA splicing.

4. Formation of triple helix DNA structures.

Recent advances in antisense technology have been focused on modifying oligonucleotides in order to offer improved nuclease resistance and increased binding affinity. These approaches include: (a) Backbone modification (b) Sugar modification, and (c) Base modification The first generation of antisense oligonucleotides was based on backbone modification in which the backbone phosphodiester bond was replaced by (a) phosphorothioates, (b) phosphorodithioates, (c) methylphosphonates, (d) phosphotriesters and (e) phosphoramidates.

The phosphorothioate[3] analogues have some potential advantages since they (i) form relatively stable duplexes with RNA (−0.1° to −1° per modification); (ii) activate RNaseH degradation; (iii) are stable to cleavage by nucleases, and (iv) are stable to base catalyzed hydrolysis. Phosphorodithioates are also quite resistant to nuclease activity however they have little advantages over phosphorothioate derivatives for antisense applications[5]. Like the phosphorothioates, methylphosphonates are normally obtained as mixtures. Although methylphosphonates do not activate RNaseH[4], they are uncharged and display (i) increased hydrophobicity, (ii) increased cell membrane permeability and (c) nuclease resistance. Regarding the O-alkylphosphotriesters(O-Et)[6], these oligomers strongly hybridize to RNA and closely conform to the helical conformation of natural β-phosphodiester DNA (self-complementary duplexes are substantially less stable[7]). The use of the latter molecules (phosphonates and triesters) in cell culture systems is limited due to the following drawbacks: (i) their low aqueous solubility; (ii) their reduced hybridization property due to high numbers of diastereoisomers formed by the chiral phosphorus atoms (phosphonates); (iii) due to their enhanced lipophilicity they are presumably targeted to intracellular lipid particles and membranes, and (iv) they are sensitive to base catalyzed hydrolysis. Phosphoramidates are quite resistant to nucleases but exhibit rather poor hybridization characteristics with DNA. This is not the case with 3'-NH phosphoramidates where substantial increase in Tm was observed.

An attractive approach in the development of antisense agents for DNA and RNA recognition is the polyamide (also known as peptide) nucleic acid (PNA) surrogates. PNAs are the first successful substitute for the sugar-phosphate backbone that have displayed equal or better binding affinity than natural DNA or RNA[8]. In contrast to the various backbone units, PNAs do not bear any structural resemblance to natural oligonucleotides. PNAs bind to an oligonucleotide sequence either via a parallel mode where the PNA amino terminus is aligned with the 5' end of DNA or via an anti parallel mode (aligned with the 3' end). Hybridization through the antiparallel mode was found to be significantly more stable than the corresponding parallel hybrid and impart an extra Tm stability of 1.45°/modification and 1°-1.2°/modification for PNA-RNA and PNA-DNA duplexes, respectively. The alternative parallel binding mode is still as stable as DNA-RNA or DNA-DNA duplexes, formed by displacing the homopyrimidine DNA stretch from the DNA duplex[9].

Transcription inhibition by PNAs can occur either by triple helix formation or by strand displacement in which the PNA displaces one DNA strand in the DNA duplex to form a PNA-DNA hybrid. Following this, by binding to a further PNA oligomer, a local (PNA)$_2$-DNA triple helix can be formed for certain sequences. Both PNA strands must be oriented either parallel or antiparallel to the DNA strand.

Two pivotal obstacles are implicated with the application of PNA systems: i) Low solubility, and ii) Diminished cell uptake. In this context and in order to cope with these hurdles several modifications yielding new types of polyamide building blocks were introduced such as depicted in the following formulae:

(Cyclo) O-PpNA

OPNA

Alpha-PNA

Proline PNA

Cyclohexy PNA

Compound A represents the original structure (Nielsen) of a PNA unit where the backbone part is composed of N-(2-aminoethyl) glycine chain and the nucleobase is tethered through an amide bond to the inner amino group. Such a highly hydrophobic system is of course of low solubility and consequently of diminished cell permeation ability. Compounds B and C and D represents a new polyamide backbone where the carboxylic moiety is replaced by phosphono (B,C) and phosphoro (D) groups to attain a more hydrophilic ribbon cord with a resistant to nucleases degradation[10]. In contrast to B, compounds C and D consist of a delta hydroxy acid backbone. This allows chain elongation by methods adopted in solid phase synthesis of oligonucleotide. Compound E (OPNA) which consist an delta amino acid was designed as an ether analogue to afford the main chain sufficient flexibility and an improved water solubility[10]. On the other hand the presence of a chiral center in the backbone structure extend chemical diversity. Structures F—H are true peptide nucleic acids analogues bearing nucleobases linked through an ethylene chain to C-1 and the amino group N of glycine and to C-4 (Trans) of proline in F,G,H respectively[11]. One of the drawbacks of a polypeptide chain as a carrier of nucleobases is ascribed to its augmented rigidity, which interrupts the spatial hybridization properties of the PNA. Compound I is a chiral Delta-amino acid PNA with a partly conformationally constrained backbone derived of cyclohexyl moiety[12].

One particular PNA analog in which the linkage of the a nucleobase to the interior amino group of the PNA unit is via an ethylene bridge has previously been described for thymine [3]. The synthesis of this derivative was accomplished from protected N,N-Bis-2-ethylamino glycine and acylisocyanate, which does not afford a general method of synthesizing other units. More importantly, it was demonstrated in that study that the positively charged PNA analog had inferior properties compared to regular PNA units (reviewed by Falkiewicz, 1999, Ref. 14). This disclosure teaches away from the use of positively charged PNA analogs altogether.

SUMMARY OF THE INVENTION

It is an object of the present invention to provide positively charged analogs of oligonucleotides. It is a more specific object of the present invention to provide positively charged peptide nucleic acid (PNA) analogs. It is a further object of the invention to provide antisense molecules comprising positively charged oligonucleotide analogs. It is yet a further object of the present invention to utilize positively charged PNA as novel delivery agents for therapeutic and diagnostic reagents, including brain delivery technologies.

According to the principles of the present invention, we herein report the synthesis of novel PNA analogs in which the linkage of the nucleobases to the interior amino group of the PNA unit is via an ethylene bridge (Scheme 1). This modification introduces positive charges along the ribbon stretch.

It is now disclosed that these positively charged sequences display enhanced water solubility and enhanced affinity to the negatively charged DNA duplex. In addition, as is known in the art this modification increases the flexibility of the side chain compared to the regular PNA (methyleneamido) surrogate.

Scheme 1

-continued

According to the principles of the present invention we provide a general procedure for the synthesis of all four bases from commercially available starting materials.

According to a first aspect of the present invention there are provided compounds of the general formula (I):

wherein, R1 is hydrogen or a protecting group suitable for protecting an amino group; R2 is hydrogen or a protecting group suitable for the protection of a carboxyl group; and Bn is a protected or unprotected, natural or non-natural nucleobase other than thymine.

Currently more preferred embodiments of the invention are compounds of formula (I) wherein R1 is hydrogen or a protecting group selected from the group consisting of Monomethoxytrityl (MMT), Dimethoxytrityl (DMTr), Fluorenyloxycarbonyl (Fmoc), tert-Butyloxycarbonyl (t-BOC), Phthalimide (Pht), and Tetrachlorophthalimide (TPht); and R2 is hydrogen or a protecting group selected from the group consisting of Methyl (Me), Ethyl (Et), Propyl(Prop), tert-Butyl (t-Bu), Benzyl (Bnz), Monomethoxytrityl (MMT).

Additional more preferred embodiments according to the present invention are compounds of the general formula (I) wherein Bn is selected from the group consisting of guanine or protected guanine (Gu); pseudo-guanine or protected pseudo-guanine (2,6-diaminopurine); adenine or protected adenine (Ad); cytosine or protected cytosine (C); pseudocytosine or protected pseudo-cytosine, pseudo-isocytosine or protected pseudo-isocytosine; uracil or protected uracil (U) and protected thymine (T).

Suitable protecting groups for cytosine and cytosine analogs include but are not limited to $R_3$=Benzoyl (Bz), Acetyl (Ac), and Diphenylacetyl (DPA).

Suitable protecting groups for adenine include but are not limited to $R_4$=Benzoyl (Bz), Acetyl (Ac), Diphenylacetyl (DPA).

Suitable protecting groups for guanine and pseudoguanine include but are not limited to those wherein the protecting group for the hydroxyl ($R_5$) is selected from the group consisting of diphenylcarbamoyl (DPC), and Benzyl (Bnz), and the protecting group for an amino group of the guanine (&) is selected from the group consisting of i-Butyryl (iBu), acetyl (Ac), and benzoyl (Bz).

Suitable protecting groups for uracil or thymine include but are not limited to $R_7$=Benzoyl (Bz), Acetyl (Ac), and Diphenylacetyl (DPA)

Most preferred compounds according to the present invention are compounds of the general formula (I) wherein Bn is selected from the group consisting of adenine or protected adenine, cytosine or protected cytosine, guanine or protected guanine. Compounds of the general formula (I) with or without protecting groups comprise positively charged PNA units having an ethylene linker between the backbone and the nucleobase, are collectively designated herein and in the claims as IP-PNA, having improved properties compared to previously known polyamide (peptide) nucleic acid analogs.

According to a second aspect of the present invention, there are provided oligomers comprising at least one peptide nucleic acid analog of the general formula (I). It will be appreciated by the skilled artisan that in such an oligomer the groups R1 and R2 are replaced by covalent bonds between adjacent monomer units.

According to another aspect of the present invention, oligomers comprising a plurality of peptide nucleic acid analogs of the general formula (I), wherein Bn may be any natural or non-natural nucleobase, including thymine are disclosed and claimed. It will be appreciated by the skilled artisan that in such an oligomer the groups R1 and R2 are replaced by covalent bonds between adjacent monomer units.

It is understood that at each occurrence the nucleobase of a given monomer is independent of the nucleobase used at any other position in the oligomer. Advantageously, according to a specific preferred embodiment the oligomers are conjugated to polyethyleneglycol to improve their pharmacokinetics.

Three currently preferred types of oligomers included within the scope of the invention are:

a) an oligomer wherein short sequences of IP-PNA units are incorporated at one or both termini (3' and/or 5') into oligomers comprising from about 10 to 30 ordinary PNA units, as depicted by the sequence:

A-A-A(n)-A-A-IP-PNA-IP-PNA-IP-PNA-X, wherein A is any known PNA unit; n is a number from about 5 to 25; IP-PNA is a compound of the general formula (I) from which all protecting groups have been removed; and X is selected from the group consisting of a free carboxylic acid, a reduced carboxylic group (alcohol) or PEG;

b) an oligomer comprising only IP-PNA units incorporated into a sequence of from about 10 to about 30 nucleobases, as depicted by the sequence:

IP-PNA-IP-PNA-IP-PNA(m)-IP-PNA-X, wherein m is number of about 6 to about 26, and X is as defined above;

c) an oligomer comprising alternating units of IP-PNA monomers and PNA monomers as depicted by the sequence:

A-IP-PNA-A-IP-PNA-(A-IP-PNA)$_m$-A-IP-PNA-X, wherein A, IP-PNA, m and X are as defined above.

Another aspect of the present invention relates to pharmaceutical compositions comprising as an active ingredient an oligomer comprising a plurality of IP-PNA units.

Another aspect of the present invention relates to use of oligomers comprising IP-PNA units as antisense molecules.

Another aspect of the present invention relates to the use of oligomers comprising IP-PNA units for translational arrest.

Another aspect of the present invention relates to the use of oligomers comprising IP-PNA units for CNS specific targeting of antisense molecules.

Another aspect of the present invention relates to the use of oligomers comprising IP-PNA units for neuronal targeting of antisense molecules.

It is now disclosed that IP-PNAs have improved properties compared to previously known Peptide nucleic acid (PNA). IP-PNAs are positively charged water-soluble molecules with improved cellular uptake as well as lysosomotropic properties, enhancing their biological properties.

In comparison with previously known PNA which require a delivery system, IP-PNA are cationic molecules that have a lysosomotropic property, therefore, they can provide unique value as vectors for transport across the BBB and intraneuronal delivery.

DETAILED DESCRIPTION OF THE INVENTION

Brain Drug Delivery Technologies

Figure 1:
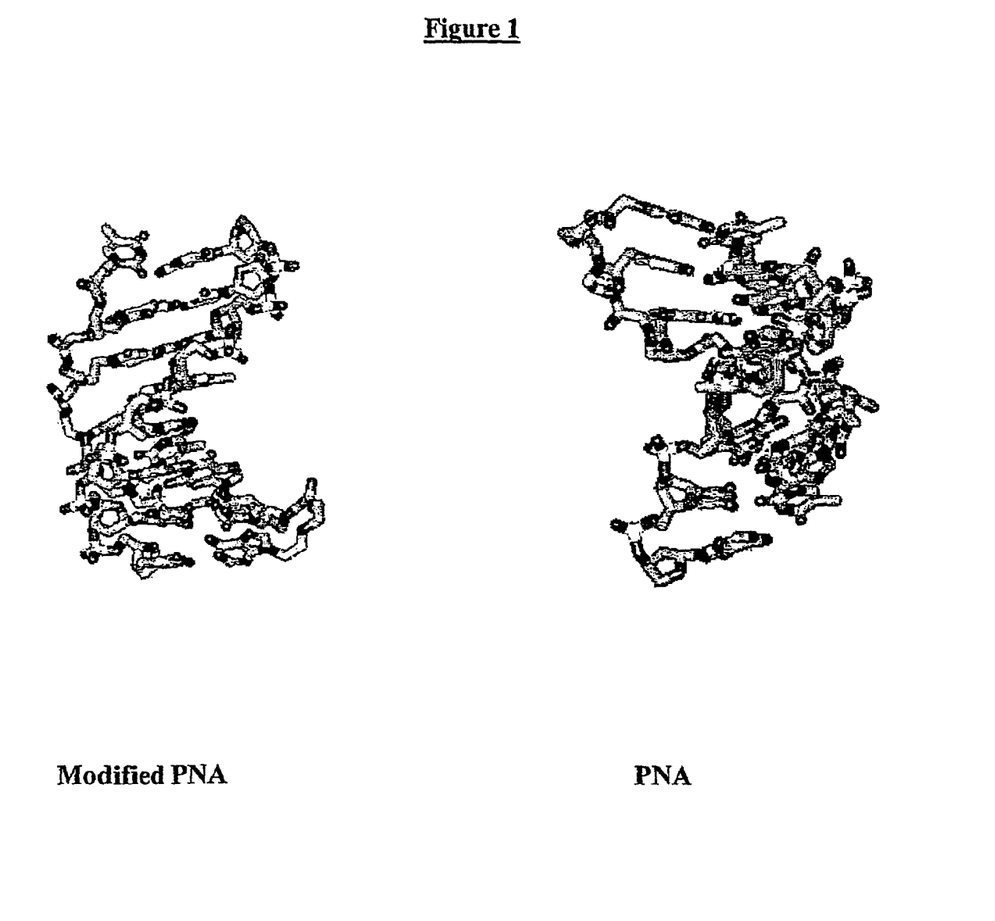
FIG. 1: Molecular modeling of PNA and IP-PNA annealing to DNA

Due to their low biomembrane permeability and their relatively rapid degradation, polypeptides and oligonucleotides are generally considered to be of limited therapeutic value. This is an obstacle in both biomedical research and pharmaceutical industry. Until recently, the intracellular administration of bioactive molecule was restricted to small hydrophobic ones, and administration of hydrophilic macromolecules required disruption of plasma membrane.

The blood-brain barrier (BBB) represents a very complex endothelial interface, which separates the blood compartment from the extracellular fluid compartment of the brain parenchyma. The BBB consists of a monolayer of polarized endothelial cells connected by complex tight junctions[15]. Several factors are known to affect the extent to which a molecule will be delivered from the blood into the brain: (1) Lipid solubility: Good correlation exists between the lipid solubility of a drug and its ability to penetrate or diffuse across the BBB[16]. (2) Size: The BBB will also prevent the passage of ionized water-soluble molecules with a molecular weight of more than 500 Da, impeding the delivery of 95% of drugs to the brain. Because of this efficient filtering activity of the BBB, the treatment of brain cancer and other neurodegenerative diseases has been relatively inefficient, as many drugs are unable to reach the brain at the necessary therapeutic levels. To overcome this problem, different methods have been developed that achieve BBB penetration[17]: (1) Disruption of the BBB by hyperosmotic shock induced by infusion of hypertonic solution (mannitol) or, by administration of biologically active agents such as bradykinin, angiotensin and RMP-7. (2) Direct intraventicular drug administration. (3) Drug modification: It is believed that the ability of a drug to cross the BBB by passive diffusion is a function of lipophilicity and hydrogen bonding potential[18]. Several strategies, such as drugs lipidization (addition of lipid-like molecules to the drug) and linkage to chemical delivery systems (CDS), have been therefore utilized. (4) Using the BBB carrier-mediated transport system for essential compounds such as amino acids and vitamins. (5) Cationic modification (such as cationized proteins) cross the BBB by absorptive-mediated transcytosis mechanism for review see 24,25). (6) Receptor-mediated transcytosis: Conjugation of therapeutic molecules to a drug-transport vector (OX26).

An alternative approach for the delivery of neuropharmaceuticals is the use of small synthetic peptides that can cross the cellular membrane efficiently (Pegelin, Penetratin). In the past five years several peptides have been demonstrated to translocate across the plasma membrane of eukaryotic cells by a seemingly energy-independent pathway. These peptides have been used successfully for the intracellular delivery of macromolecules with molecular weights several times greater than their own. For example, Tat is a transcription factor involved in the replication of HIV. It has been found that one of its functional domains 49-58 amino acids) is responsible for nuclear import. Tat appears in a secreted form, which is then re-internalized by live cells in a time and concentration-dependent manner. In addition to its ability to cross cell membrane, it has been demonstrated that a Tat-derived short peptide could cross the blood brain barrier and deliver active protein into the brain. The potential of this approach (peptide-vector strategies) as an effective delivery system for transporting drugs across the BBB has been demonstrated in animal models by an in situ brain perfusion model in rats and by intravenous injection into mice[19,20].

Antisense Delivery into the Brain

Antisense oligodeoxynucleotides (ODNs) are negatively charged high molecular weight molecules (the molecular weight of 14 nucleic acids is about 5Kda). Unmodified (naked) ODNs and PNAs are unable to cross the BBB in vivo. Therefore, it is necessary to administer them directly into either the cerebral ventricles or a particular intracerebral site. Apart from the huge technical limitations (invasive procedure), unmodified ODNs are rapidly degraded in the brain while phosphorothioate (PS)-ODNs are rapidly cleared via cerebrospinal fluid bulk flow and consider to be neurotoxic at therapeutic concentration greater than 1 $\mu M^{24,25}$). Therefore, if antisense molecules are to be effective therapeutics for CNS disorders, it is necessary to conjugate them to delivery systems. The delivery systems develop so far were limited by:
1. Low efficiency in vivo (ODN-encapsulated liposomes) 2. Combination of cytotoxicity and in vivo instability in the case of ODN-polylysine conjugates 4. Rapid degradation. 5. Rapid plasma clearance rate. A strategy that was develop recently for the delivery of large molecule into the brain is based on conjugation of avidin-cationized albumin or the OX26 monoclonal antibody directed to the transferrin receptor[21-22]. PNA were also conjugated to OX26/strepavidin vector[23]. This modification increases by at least 28 fold peptide entry into the brain reaching a level comparable to that for morphine, a neuroactive small molecule (0.1% of injected dose per gram of brain). Moreover, PNAs retain affinity for target RNA despite conjugation to the BBB drug targeting system. Apart from complexity and the potential immunogenic properties of such a vector, this approach will unlikely be active in vivo without an endosomal release function built into it[26]. Other new technologies still need to overcome some major obstacles. Factors such as metabolic stability, plasma protein binding, intracellular compartmentation and cell membrane transport need to be considered if the promise of antisense therapeutics to become a neuropharmacology reality.

Brain Specific Antisense

Our approach to the development of CNS-oriented gene arrest technology is based on several findings (for additional references on BBB transport: see 27-31):

1 PNA-based antisense should be delivered into the brain either via absorptive mediated transcytosis or via carrier peptides (modified/or unmodified).

2 Positively charged surface proteins adhere to the negatively charged cell surface, resulting in improved transport efficiency. Cationic molecule can induce leakage from endosomes, therefore, it enhances trans-membrane penetration and localization to the subcellular compartment containing the nucleic acid targets.

3 For drug with a low permeability, where the extraction rate from blood plasma into the organ during a single capillary passage is below 20%, uptake is not limited by blood flow. Therefore the brain tissue accumulation in a phase of unidirectional uptake can be expressed as: $C_{brain}=PS \times AUC$ (PS=brain capillary permeability surface area product. AUC=area under the plasma concentration time curve)

4 To improve pharmacokinetic properties (reduced uptake by kidney and liver will result in higher plasma AUC, and will increase $C_{brain}$), and masked/reduced immunogenicity, conjugation with poly-ethyleneglycol (PEG) is necessary.

5 Only limited numbers of antisense molecules will cross the BBB. Therefore, to achieve therapeutic effect it is necessary to increase the antisense potency.

6 The final product should be simple for synthesis and modifications.

7 Relative specificity: Similar to certain small molecules, and if effort of optimizing BBB entry, the final product (lead compound) may be specific enough therapeutically even though not as specific as the original PNA.

Improved PNA-Based Antisense Molecules (P-Antisense)

According to the principles of the present invention we now provide improved PNA analogs in which the linkage of the nucleobases to the interior amino group of the PNA unit is via an ethylene bridge. This modification introduces positive charges along the ribbon stretch. These positively charged sequences would display enhanced water solubility. In addition, this modification increases the flexibility of the side chain compared to the methyleneamido surrogate.

As with cationic albumin it is expected that this molecule will cross the BBB via absorptive-mediated transcytosis mechanism (see ref.31). The thymine derivative was already been synthesized by Hyrup et al.[14] from protected N,N-Bis-2-ethylamino glycine and acylisocyanate. In the next section we outline a general procedure for the synthesis of all four bases from commercially available starting materials.

The hybridization properties of tertiary amine-modified PNA (ethT) were partially examined by Hyrup et al.[14]. The modified PNA was incorporated in the middle of a PNA decamer and the effect of this modification on Duplex motif and Triplex motif were examined. It was found that this modified PNA decreased the stability of PNA-DNA complexes. However, despite the lower stability, the thymine in the ethT analog specifically recognized the complementary adenine in the DNA strand since mismatches cause a further decrease in Tm. We have synthesized the other nucleotides as well, and developed a simple procedure for the synthesis of these modified PNAs.

It is accepted that positively charge tertiary amines will cross the BBB presumably by absorptive mediated transcytosis. These modified PNA (IP-PNA) are going to be used as "specific carriers" for unmodified PNA (A) and also to improve the water solubility of the molecules. Cationic molecules are normally cleared rapidly by the liver. Therefore, in order to improve their pharmacokinetic properties the antisense may advantageously be conjugated to polyethylene glycol (PEGylated). According to one embodiment of the present invention it is preferable to use PEG with molecular weights in the range of 2000-3400, though other ranges may also be utilized. This is a known technique that reduces hepatic clearance. Other conjugates or techniques may be used to achieve the same objective of reduced clearance.

Three particular embodiments are currently most preferred:

1. Flag approach: Short sequence (5-10) of IP-PNA units will be incorporated to 5-25 mer PNA sequence 3' and/or 5' position. The IP-PNA will be located at these positions to reduce the possibility that it affect the PNA-mRNA/DNA stability.

A-A-A-A . . . A-A-IP-PNA-IP-PNA-IP-PNA-X

2. Charge approach: Complete IP-PNA sequence its hybridization properties were never tested before. However, based on our computerized modeling this modified PNA does have antisense properties.

IP-PNA-IP-PNA-IP-PNA . . . IP-PNA-X

3. Alternating approach: An alternate approach where IP-PNA will be incorporate into the PNA sequence alternately.

A-IP-PNA-A-IP-PNA-A . . . A-IP-PNA-A-WP-PNA-X

Backbone derivatization. Synthetic procedures utilizing the regular PNA backbone are well documented in the literature. In the case of preparing our new type of PNA we have tried to alkylate the interior secondary amine of the protected backbone N-2-monomethoxytrityl, 2-aminoethyl, ethyl glycinate with iodo and bromo ethanol under basic conditions. Changing the ratio of the reactant, the base, and reaction temperature yielded poor results. This led us to employ another commercially available staring material: N,N-(2-Hydroxyethyl),2-aminoethylamine (Compound 3 of scheme 2 below), which comprises 2 amino groups (a primary and a secondary), and a tethered hydroxyl moiety. The synthetic viewpoint of constructing the backbone (Compound 5 of scheme 2 below) is first to protect the distal amino group and successively to alkylate the internal amine with tert-butyl-bromoacetate.

BOC disclosed only low selectivity to the primary amine over the secondary and the reaction to protect the distal amino group of 4 (Compound 4 of scheme 2 below) gave a mixture of mono and di-BOC products. The Fmoc protecting group was highly selective toward the primary amine, however it was cleaved under the Mitsunobu reaction conditions. Two protecting groups proven to be of high selectivity to primary amines and ease to introduction are the monomethoxytrityl (MT or NMt) and the phthalimido protecting groups (Pht). MMT is cleaved with high yield within few minutes by low concentration of TFA while Phth group is cleaved by hydrazine (or hydrazine derivatives) or primary amines (as methyl amine or ethylene diamine) within a long period of time at low temperatures (24-48 hrs at r.t.) or within a shorter period of time at elevated temperatures (2-3 hrs at 60-70° C.).

We decided to proceed with both of these currently preferred protecting groups.

The Synthesis of the PNA units is depicted in Scheme 2. Firstly, the terminal amino group of 3 was protected by monomethoxytrityl (MMT) to result compound 4. The internal amino group of compound 4 was then alkylated by ethyl (t-Bu) bromo acetate to attain 5

Scheme 2

The alkylation of 4 by ethyl bromoacetate (R=Et) is concomitant with a substantial amount of a by product derived from the nucleophilic attack of the free hydroxyl group reside on the side chain, on the carbonyl group to form a six member ring lactone. In Order to circumvent this reaction the t-Butyl ester was introduced.

The intra-molecular transesterification was proved using $^1$H-NMR. The characteristic chemical shifts of the ethyl ester (—OC$\underline{H}_2$—C$\underline{H}_3$) of the desire backbone disappeared and the chemical shifts of the methylene groups of HO—C$\underline{H}_2$CH$_2$—N were shifted from 3.7 to 4.3 ppm. Due to this side reaction, the tert-butyl-bromoacetate was used for the alkylation of the secondary amine. The desired backbone (5) was purified on silica gel column chromatography. The stability of the tert-butyl ester was followed by $^1$H-NMR for several days at R.T.

Derivatization of Nucleobases.

Essentially, the nucleobases can be attached to the designed backbone by three of the following methods: i) Replacing the linked hydroxyl group on the backbone structure by a bromide group, and subsequently alkylating the nucleobases at the appropriate positions, employing strong bases as NaH, $K_2CO_3$ or $CsCO_3$ in dry solvents mainly dry DMF, ii) to apply a similar procedure to the above but instead of using the alkyl bromide modification, to transform the hydroxyl group into a mesylate ester, and iii) alkylating the protected nucleobase with the 2-hydroxy ethyl group of compound (5) using Mitsunobu reaction conditions. All the three methods require special protecting groups on the reactive site of the nucleobases. Since our backbone consists of a tertiary amine that can be alkylated under the experimental conditions we decided to employ merely the Mitsunobu reaction. The conditions for the attachment of the first three nucleobases (A, T, G) are well documented.

In this regard the adenine (A) was used with no protection of the $N^6$ exocyclic amine, since protection at this position decreases the regioselective alkylation of the $N^9$ under Mitsunobu conditions. To increase the solubility of the non-protected adenine the reaction mixture was warmed to 40° C. $N^6$ of the adenine should be protected before the chain assembly since this exocyclic amine can interfere with the coupling reactions. Thus after the attachment of the unprotected adenine benzoyl group was used as to this aim.

In the case of thymine (T), in order to direct the alkylation to $N^1$, $N^3$ should be protected. Thymine (T) was converted to $N^3$-Bz-T (8) by treatment of (T) with excess of benzoyl chloride in pyridine for 24 h. This actually yielded the N',$N^3$ di-benzoylated product (7). The N'-benzoyl group was selectively cleaved using mild basic conditions by in situ adding water to the reaction vessel. Stirring the aqueous solution for 8-10 hrs cleaved ultimately all the $N^1$-benzoyl group and gave rise to compound (8) (Scheme 3). The desired mono protected $N^3$-benzoyl thymine (8) was collected in high yield after washing the excess of benzoic acid with ether.

Scheme 3

The product (9) was collected and subsequently the $O^6$ carbonyl was carbamoylated by diphenyl carbamoyl chloride. The final product (10) was obtained after evaporation of the solvent and treatment of the residue with ethanol-water mixture (1:1) under reflux to hydrolyze the $N^9$ acetamido group.

In the case of cytosine, the commonly used procedure is to ablylate the $N^1$ position of the cytosine, after protecting the $N^4$ position through benzoylation, using the above mentioned method (i), of alkyl halide (in our case the ethyl bromide residue on the monomer backbone) with strong base as NaH or cesium carbonate. Kuwahara and his co-workers[10b] tried to apply Mitsunobu reaction to the $N^4$-bezoylated cytosine with no success. Part of the explanations provided referred to the pure solubility of the $N^4$-bezoylated cytosine in dry THF. We intended to solve this obstacle by using a more lipophilic protecting group. Diphenylacetyl (DPA) was chosen to acquire this aim. In conjunction with this, the amino group $N^4$ of Cytosine (C) was protected by diphenylacetyl chloride in pyridine in high yield and purity (Scheme 5).

Scheme 5

All the protected bases (G, T, and C) reacted with the alcohol (5) under standard Mitsunobu condition to give products: 12G, 12T and 12C. The attachment of $N^4$-DPA-cytosine was accomplished successfully with high yield. Adenine was applied to the Mitsunobu reaction with no any protection. Acylation of the $N^4$ amino group of adenine took place succeeding the attachment of adenine to the PNA backbone.

Scheme 6

The Fmoc derivative of the free acid was achieved by removal of the MMT and the t-butyl protecting groups of compounds 12A, 12T, 12G, and 12C by TFA in $CHCl_3$ or in DCM or by HBr/ACOH 10% followed by the treatment with 9-fluorenylmethylchloro formate (Fmoc-Cl) or 9-fluorenylmethyl succinimidyl carbonate (Fmoc-OSu).

Scheme 7

All intermediates and the final products were characterized by $^1$H NMR and high resolution mass Spectroscopy.

EXAMPLES

Synthetic Examples

I) PNA Backbone Synthesis:

NNN-(2-Hydroxyethyl),(2-(monomethoxytrityl) aminoethyl) tert-butyl glycinate (5)

NN-(2-Hydroxyethyl),(2-monomethoxytrityl) Amino) Ethane (4)

20 ml, (200 mmol) of (2-hydroxyethyl)ethylene diamine (HEED) (3) and (30 ml, 0.2 mmol) of triethylamine (ITA) were dissolved in 100 ml of dichloromethane. The mixture was cooled in ice-sodium chloride bath to 0° C. While vigorously stirred, (15 g, 48.57 mmol) of MT-Cl in 50 ml $CH_2Cl_2$ (DCM) were added drop wisely over one hour. The mixture was stirred for more 2 hrs at 0° C. then allowed to elevate to room temperature and stirred for further 20 hrs. To eliminate the excess of the BEED the organic layer was washed with 3×100 ml water. The organic phase was dried over anhydrous $Na_2SO_4$, the solid was filtered off and the solvents were evaporated to dryness. The yellowish oil was used with no further purification.

$^1$H-NMR (CDCl$_3$) δ:

7.49-7.15 (m, 12H, MMT); 7.14-6.79 (dd, 2H, MMT); 3.76 (s, 3H, —OC$\underline{H}_3$); 3.61-3.58 (t, 2H, HO—C$\underline{H}_2$—); 2.75-2.68 (m, 4H, —(C$\underline{H}_2$)$_2$—NH) 2.3-2.26 (t, 2H, —C$\underline{H}_2$—NH-MMT);

The above product was dissolved in 100 ml of dichloromethane and (7 ml, 50 mmol) of triethylamine was added. The mixture was cooled to 0° C. and (8.57 ml, 58 mmol) of tert-butyl bromoacetate in 20 ml $CH_2Cl_2$ were added drop wisely. The mixture was stirred at r.t. for 24 hrs. The organic phase was washed with 3×100 ml water and dried over $Na_2SO_4$. After filtering off the solid the solvents were evaporated to dryness under reduced pressure. The yellowish viscous product was purified on silica gel column chromatography. The desired product was obtained as colorless viscous oil. Eluting solvents: 30-50% ether in petroleum ether.

$^1$H-NMR (CDCl$_3$):

7.48-7.45 (dd, J$_{1-3}$=8.4, J$_{1-4}$=1.2 Hz, 2H, MMT); 7.38-7.36 (d, J=7.8 Hz, 2H, MMT); 7.30-7.14 (m, 8H, MMT); 6.85-6.79 (dd, J$_{1-3}$=15.3 Hz, J$_{1-4}$=2.1 Hz, 2H. MMT); 3.77 (s, 3H, H$_3$CO—); 3.59-3.56 (t, J=5.1 Hz, 2H, HO—C$\underline{H}_2$—); 3.13 (s, 2H, N—C$\underline{H}_2$—COO—); 2.79-2.71 (m, 4H, N(C$\underline{H}_2$)2-); 2.22-2.18 (t, J=6 Hz, 2H, —C$\underline{H}_2$—NH-MMT); 1.41 (s, 9H, tert-But).

II) Nucleobase Protection:

(1) Thymine:

To a suspension of thymine (T) (5 g, 40 mmol) in 40 ml of dry pyridine, (15 ml, 130 mmol) of Bz-Cl were added and the reaction was stirred over night at room temperature. TLC indicated the end of the reaction. The reaction mixture was cooled to 0° C. and 30 g of ice were added in fractions. The reaction temperature was elevated to r.t. and the stirring continued for 8-10 more hrs. The solvent was removed under reduced pressure. 200 ml of ether and 100 ml of water were added to the viscous residue, while vigorous stirring. The white precipitate was filtered and washed with 100 ml of ether.

TLC (10% MeOH/CHCl$_3$) diBz-T RF=0.95

Bz-T Rf=0.5

$^1$H-NMR (CDCl$_3$):

7.96-7.93 (dd, J$_{1-3}$=11.4 Hz, J$_{1-4}$=1.2 Hz, 2H, 2H o to CO); 7.70-7.65 (m, 1H, $\underline{H}$ p to CO) 7.54-7.49 (m, 2-$\underline{H}$, $\underline{H}$2 m to CO); 7.03 (s, 1H, $\underline{H}$-(C6)); 1.91 (s, 3H, $\underline{H}_3$C—(C5)).

(2) Guanine:

A suspension of (5 g, 33 mmol) of guanine in 100 N-methy-2-pyrrolidinone NMP) and 20 ml acetic anhydride was heated to 150° C. for 3 hrs. The clear solution was stirred at room temperature for 24 hours. The precipitate was collected by filtration and washed with acetone. The N$^9$,N$^2$-diacetylated guanine (9) was dried and identified by $^1$H-NMR.

M.P.=Decomp. 270° C.

$^1$H-NMR (DMSO-d$_6$):

12.1 (bs, 1$\underline{H}$—(N)), 8.53 (s, 1H, $\underline{H}$—(C8)); 2.91 (s, 3H, $\underline{Ac}$—(N9)); 2.31 (s, 3H, —(N2-COC$\underline{H}_3$)). (5 g, 21.25 mmol) of (9) were suspended in 100 ml of dry pyridine and excess of diisopropyl ethylamine (DIEA). Then (5.91 g, 25.51 mmol) of diphenylcarbamoyl chloride ere added in portions. The reaction mixture turned orange immediately. Stirring continued for 2 hrs at r.t. then 20 ml if ice-cold water were added. The mixture was stirred for 10 minutes more and solvent was removed under reduced pressure. 100 ml of ethanol and 100 ml of water were added and the mixture was reflexed for 1.5 hr. After cooling to the room temperature, vigorous stirring continued for over night. The desired product (10) was collected by filtration and washed with 50 ml of ethanol, dried and characterized.

M.P.=185° C.

$^1$H-NMR (DMSO-d$_6$):

10.7 (s, 1H, $\underline{H}$—(N2)); 8.55 (s, 1H, $\underline{H}$—(C8)); 7.61-7.38 (m, 10H, aromatic); 2.28 (s, 3H, —COC$\underline{H}_3$).

(3) Cytosine:

N$^4$-(Diphenyl acetyl)cytosine

To stirred suspension of (3 gr, 27 mmol) of cytosine (C) in 30 ml of dry pyridine at room temperature (6.85 g, 29.7 mmol) of diphenylacetyl chloride were added in portions. The reaction mixture was stirred at room temperature over-night. TLC indicated the end of the reaction. 2 ml of water was added and the solvent was evaporated under reduced pressure. 100 ml of water were added to the residue and the mixture was stirred vigorously for 30 minutes. The desired product (11) was precipitate and filtered. The white precipitate was washed with 100 ml of ether and dried.

$^1$H-NMR (DMSO-d$_6$):

11.43 (bs, 1H, H—(N4)); 7.95-7.93 (d, J=6.9 Hz, 1H, H—C(5)), 7.44-7.42 (m, 10H, aromatic); 7.26-7.24 (d, 1H, H—(C6)); 5.48 (s, 1H, H—(C-diphenyl)).

III) Nucleobase Attachment:

The three nucleobases (O$^6$-DPC, N$^2$-Ac-G, N3-Bz-T, A and N$^4$-DPA-C) were attached to the backbone using Mitsunobu conditions. The nucleobases were dried in a dessicator under vacuum over P$_2$O$_5$ and KOH.

General Procedure for the Nucleobase Attachment:

(20 mmol) of the backbone were dried by successive co-evaporation 3×50 ml of dry toluene. The dried backbone was dissolved in 200 ml dry and fresh THF. To the reaction vessel, under inert atmosphere (18.3 mmol) of the appropriate nucleobase (O$^6$-DPC, N$^2$-Ac-G; N$^3$Bz-T; A; N$^4$-DPA-C) and 20 mmol of triphenylphosphine (TPP) were added. The mixture was cooled to 0° C. To the stirred mixture, 1.1 eq of diethylazodicarbixylate (DEAD) were added drop wise over a period of one hrs. The reaction mixture was stirred at R.T. (for adenine at 40° C.) for 24 h and solvents were evaporated to dryness. The desired product was purified on silica gel column chromatography. Eluting solvents: For N$^3$-Bz-T: petroleum ether→27% ether/petroleum ether; For A, eluting solvents ether→26% of methanol/ether; for G: ether→4% methanol/ether and for DPA-C: petroleum ether→27% ether/petroleum ether General Procedure for the conversion of 12(A,C,G,T) to 13(A,C,G,T)

a) 0.1 mol of TFA is added dropwise to a cold solution of 2.5 mmol of 12(ACGT). and 0.25 ml of triisopropylsilane in 5 ml of DCM. The reaction mixture is stirred for 48 h at room temperature and evaporated to dryness in cold. The residue is dissolved in 10% aq. NaHCO$_3$ (15 ml) and acetonitrile (15 ml). The solution is cooled in an ice bath followed by an addition of 3.0 mmol 9-fluorenylmethyl succinylimidyl carbonate (Fmoc-OSu) or 9-fluorenylchloro formate (Fmoc-Cl) in acetonitril (7 ml). The reaction mixture is stirred for 12 h at room temperature and evaporated to dryness. The residue is dissolved in water (10 ml) and the aqueous layer is washed with diethyl ether (3×10 ml) and adjusted to pH 7 with 10% of KHSO$_4$. Subsequently, two layer are formed. The aqueous upper layer is discarded and the lower layer is washed with H$_2$O (5 ml) and dried to afford a white solid. In the case of N$^3$ benzoyl Thymine, TFA cleaved part of the benzoyl protecting group and the two product formed were separated on column chromatography (silica, eluent 3-5% ethanol/diethylether)

Two alternative variations are also effective b) Cleavage of the protecting groups (MMT and t-But) by allowing 10% HBr/CH$_3$COOH to react for 1 h, and c) After phase separation the lower layer is extracted with DCM.

General Procedure for the Conversion of 12(A,C,G,T) to 12(AN,CN,GN,TN)

To 2.0 mmol of 12 (ACGT) and 0.25 ml of triisopropylsilane 20 ml of TFA in DCM (2%) is added dropwise in cold (ice bath) The reaction mixture is stirred for 30 min at and evaporated to dryness in cold. The residue is dissolved in 20 ml of DCM and washed with 10% aq. NaHCO$_3$ (15 ml) followed by 5 ml of H$_2$O. The organic phase is dried by MgSO$_4$ and evaporated The remaining solid is applied to column chromatography (silica, eluent: ethylacetate to 10% methanol/ethylacetate). In the case of 12GN triturated several times with diethylether result the pure product.

t-But-N-{(3-N-benzoyl thymine-1-yl)ethyl}-N-(2-Mmt-aminoethyl) glycinate (12T)

$^1$H-NM (CDCl$_3$):

7.93-7.91 (d, 2H, N$^3$-Benz); 7.59-7.61 (t, 1H, N$^3$-Benz); 7.47-7.71 (m, 15H, MMT+N$^3$-Ben+1H—(C6)), 6.81-6.78 (d, 2H, MMT); 3.76 (s, 3H, —OCH$_3$); 3.69-3.68 (t, 2H, —CH$_2$—(N1-T)); 3.07 (s, 2H, CH$_2$—COO-tert-But); 2.88-2.7 (m, 4H, N—(CH$_2$)$_2$—); 2.24-2.23 (m, 2H, —CH$_2$—NH-MMT); 1.75 (s, 3H, C(4)CH$_3$); 1.41 (s, 9H, tert-But).

MS, m/e 702.9 (M$^+$), calc: 702.85

M.P.=122° C.

TLC (5% Methanol/CH$_2$Cl$_2$) RF=0.75 t-But-N-{(6-O-diphenylcarbamoyl-3-N-acetylguanin-9-yl)ethyl}-N-(2-Mmt-aminoethyl) glycinate (12G)

$^1$H-NMR (CDCl$_3$):

8.03 (s, 1H, H—(C8)); 7.7-7.13 (m, 22H, MMT+DPC); 6.79-6.76 (d, 2H, MMT); 4.12-4.06 (t, 2H, CH$_2$—(N9)); 3.74 (s, 3H, OCH$_3$); 3.07 (s, 2H, —CH$_2$—COO—); 2.99-2.95 (t, 2H, —CH$_2$—N—); 2.83-2.79 (t, 2H, —CH$_2$—N—); 2.53 (s, 3H, N2-Ac); 2.21-2.17 (t, 2H, —CH$_2$—NH-MMT); 1.42 (s, 9H. tert-But).

MS, m/e 861 (M$^+$), calc: 861.01

TLC (5% Methanol/CH$_2$Cl$_2$)

RF=0.64

M.P.=50-53° C.

t-Butyl-N-(2-Mmt-aminoethyl)-N-(adenine-9-yl-ethyl) glycinate (12A)

$^1$H-NMR (CDCl$_3$):

8.27 (s, 1H, H—(C8)); 7.87 (s, 1H, H—(C2)); 7.43-7.13 (m, 12H, MMT); 6.79-6.76 (d, 2H, MMT); 5.7 (bs, 2H, H$_2$—(N2)); 4.15-4.11 (t, 2H, —CH$_2$—(N9)); 3.76 (s, 3H, —OCH$_3$); 3.0 (s, 2H, —CH$_2$—COO—); 3.0-2.96 (t, 2H, —CH$_2$—N—); 2.82-2.78 (t, 2H, —N—CH$_2$—); 2.19-2.16 (t, 2H, —CH$_2$—NH-MMT); 2.06 (bs, 1H, —NH-MMT); 1.39 (s, 9H, tert-But).

MS, m/e 607.9 (Me), calc: 607.75

TLC (5% Methanol/CH$_2$Cl$_2$) RF=0.4

M.P.=60-62° C.

t-But-N-{(4-N-(diphenylacetyl) cytosine-1-yl)ethyl}-N-(2-Mmt-aminoethyl)glycinate (12C)

$^1$H-NMR(DMSO-d$_6$):

1.4 (bs, 1H, H—(N4)); 8.03-7.95 (d, 1H, H—(C6)); 7.8-6.75 (m, 14H, MMT), 6.75 (m, 10H, DPA, +H—(C5)); 5.65 (s, 1H, H-(DPA)); 3.95-3.9 (t, 2H, CH$_2$—(N1)); 3.76 (s, 3H, —OCH$_3$); 3.0 (s, 2H, —CH$_2$—COO—); 2.83-2.79 (t, 2H, —CH$_2$—N); 2.76-2.74 (t, 2H, —N—CH$_2$); 2.19-2.16 (t, 2H, —CH$_2$—NH-MMT); 1.39 (s, 9H, tert-But).

MS, m/e 778.1 (M$^+$), calc: 777.96

TLC (5% Methanol/CH2Cl2) RF=0.67

TLC (5% Methanol/CH2Cl2) RF=0.67

N-{(3-N-benzoyl thymine-1-yl)ethyl}-N-(2-Fmoc-aminoethyl) glycinate (13T)

$^1$H NMR(CDCl$_3$)

7.9-7.90 (d, 2H, Bz); 7.2-7.67 (m, 8H, Fmoc+3 HBz); 7.12 (s, 1H, H—C6); 4.38 (bd, 2H, Fluo-CH$_2$); 4.19 (bt, 1H, Fluo-H); 3.4, (s, 2H, CH$_2$—COOH); 3.79 (,bt, 2H, N—CH$_2$—CH$_2$); 3.22 (,bt, 2H, N—CH$_2$—CH$_2$); 2.90 (bt, 2H, CH$_2$NCH$_2$), 2.79 (bt, 2H, CH$_2$NCH$_2$); 1.84 (s, 3H, C5'CH$_3$);

MS, m/e 596 (M$^+$), calc: 596.23

M.P.=113° C.

N-{(4-N-(diphenylacetyl) cytosine-1-yl)ethyl}-N-(2-aminoethyl) glycinate (13C)

$^1$H NMR (DMSO-d$_6$)

8.02-7.19 (m, 19H, H—C$_6$+Fmoc+DPA); 5.65 (bd, 1H, C5-H); 5.19 (s, 1H, (Ph)$_2$-CH); 4.25 (bd, 2H, Fluo-CH$_2$); 4.19 (bt, 1H, Fluo-H); 3.83 (,bt, 2H, N—CH$_2$—CH$_2$); 3.50 (,bt, 2H, N—CH$_2$—CH$_2$); 3.41, (s, 2H, CH$_2$—COOH), 2.88 (bt, 2H, CH$_2$NCH$_2$), 2.66 (bt, 2H, CH$_2$NCH$_2$);

MS, m/e 672 (M$^+$), calcd: 671.74

MP.=144-150° C.

t-But-N-{(6-O-diphenylcarbamoyl-3-N-acetylguanin-9-yl)ethyl}-N-(2-aminoethyl) glycinate (12GN)

$^1$H NMR (CDCl$_3$)

7.58 (s, 1H, C8-H), 7.40-7.20 (m, 10H, DPC); 4.18 (,bt, 2H, N9-CH$_2$); 3.60 (,bm, 2H, NH$_2$—CH$_2$); 3.20, (s, 2H, CH$_2$—COOH); 2.98 (bt, 2H, CH$_2$NCH$_2$), 2.60 (bt, 2H, CH$_2$NCH$_2$); 1.62 (s, 3H, C$_2$NHCOCH$_3$): 1.19 (s, 9H, t-But)

MS, m/e 589 (M$^+$), calcd: 588.86

The Mass Spectra Results:

| Monomer | Calculated MW | Found | Deprotected | Calculated | Found | MMT |
|---|---|---|---|---|---|---|
| 12-T | 702.85 | 702.9 | Backbone-T | 430.5 | 431.1 | 273.3 |
| 12-A | 607.75 | 607.9 | Backbone-A | 335.40 | 336.1 | 273.3 |
| 12-G | 861.01 | 861 | Backbone-G | 588.66 | 589.3 | 273.3 |
| 12-C | 777.96 | 778.1 | Backbone-C | 505.61 | 506.1 | 273.3 |
| 13-T | 596.63 | 597 | | | | |
| 13-C | 671.74 | 672 | | | | |
| 12GN | 588.86 | 589 | | | | |

Alternative Protecting Groups and Synthetic Schemes

Another protecting group introduced to the terminal amino constituent of the monomer backbone was the Phthalimido group. The general synthetic method is depicted in the following scheme.

R=(a)-Methyl (Me)., (b)Ethyl (Et)., (c)-Propyl(Prop)., (d)tert-Butyl (t-Bu)., (e)-Benzyl (Bnz)., (f)-MMT., (g) Hydrogen(H)., X=H, Cl., The final product was attained via three step reaction. The first step describe the attachment of the Phthalimido protecting group to the external amino group of aminoethylamino ethanol to get 14.

The second step involves the reaction of 14 with alkyl (R) bromoacetate to form Alkyl (R)-N,N-2-hydroxyethyl), (2-Phthalimidoaminoethyl) glycinate (15). The third step present the coupling of the protected nucleobases to 15 to yield compounds 16(ATCG).

A General Method for the Preparation of 2-(2-Phthalimidoethylamino)ethanol (14)

10.4 g (0.1 mol) of N,N-(2-hydroxyethyl),ethyl amine and 22 g (0.1 mol) of N-ethoxycarbonyl phthalimide were dissolved in 50 ml of $H_2O$ and stirred for 2 hours. The reaction mixture was lyophilized and the solid product washed with methanol (40 ml). The remaining white solid (Compound 14) was collected and dried.

A General Method for the Preparation of Alkyl(R)-N,-(2-Phthalimido-aminoethyl),N-2-hydroxyethyl) glycinate (15)

To 11.7 g (50 mmol) of 2-(2-Phthalimidoethylamino)ethanol and 8.75 ml (58 mmol) t-butyl-bromoacetate in 100 ml DMF, 7 g (50 mmol) were added. The reaction mixture was vigorously stirred for 1 week. Subsequently the solvent was removed under vacuum, the viscous oil left dissolved in 200 ml of chloroform and washed 2× with water. The aqueous phase was extracted with 200 ml of chloroform and the combined organic phase was dried with sodium sulfate filtered and evaporated to afford pale yellow oil. Purification was carried out by chromatography (solid phase-silica, eluent—$CHCl_3$). Yield 60%

Nucleobase Attachment:

As previously been described, the four nucleobases ($O^6$-DPC, $N^2$-Ac-G; N3-Bz-T; A; and $N^4$-DPA-C) were attached to the backbone (15) via Mitsunobu reaction.

t-But-N-{(3-N-benzoyl thymine-1-yl)ethyl}-N-(2-Phthalimido-aminoethyl) glycinate (16T)

$^1$H-NMR ($CDCl_3$):
7.99-7.48 (m, 9H, Ar); 7.25 (s, 1H—(C6)); 3.78 (bt, 4H, —CH$_2$—(N1-T)+CH$_2$-(Pht-N—); 3.35 (s, 2H, CH$_2$—COO-tert-But); 2.98 (m, 4H, (CH$_2$) N—(CH$_2$)); 1.79 (s, 3H, C(4)CH$_3$); 1.41 (s, 9H, tert-But).
MS, m/e 561.1 (M$^+$), calcd: 560.6
M.P.=152° C.

t-But-N-{(6-O-diphenylcarbamoyl-3-N-acetylguanine-9-yl)ethyl}-N-(2-Phthalimido-aminoethyl) glycinate (16G)

$^1$H-NMR ($CDCl_3$):
8.19 (bs, 1H, C2-NH) 7.98 (s, 1H, H—(C8)); 7.78-7.32 (m, 14H, DPC+Pht); 4.19 (bt, 2H, CH$_2$—(N9)); 3.70 (bt, 2H, PhtNCH2); 3.19 (bt, 2H, —CH$_2$—N—); 3.02 (bt, 2H, —CH—N—); 2.60 (s, 2H, —CH$_2$—COO—); 1.64 (s, 3H, N2-Ac: 1.22 (s, 9H. tert-But).
MS, m/e 719.2 (M$^+$), calcd: 718.29
M.P.=decomp.

t-Butyl-N-(2-Phthalimido-aminoethyl)-N-(adenine-9-yl-ethyl) glycinate (16A)

$^1$H-NMR ($CDCl_3$):
8.14 (s, 1H, H—(C2)); 7.88 (s, 1H, H—(C8)); 7.8-7.71 (m, 14H, Pht); 5.85 (bs, 2H, C6-NH$_2$); 4.20 (t, 2H, —CH$_2$—(N9)); 3.69 (bt, 2H, PhtNCH$_2$); 3.35 (s, 2H, —CH$_2$—COO—); 3.19 (t, 2H, —CH$_2$—N—); 3.01 (t, 2H, —N—CH$_2$—); 1.42 (s, 9H, tert-But).
MS, m/e 466.2 (M$^+$), calcd: 465.21
M.P.=151° C.

t-But-N-{(4N-(diphenylacetyl) cytosine-1-yl)ethyl}-N-(2-Phthalimido-aminoethyl) glycinate (16C)

$^1$H-NMR ($CDCl_3$):
9.92 (bs, 1H, C4-NH); 7.15 (bd, 1H, H—(C6)); 7.92-7.21 (m, 14H, Pht+DPA); 3.85 and 3.72 (dt, 4H, CH$_2$—(N1)+Pht-CH$_2$); 3.0 (s, 2H, —CH$_2$—COO—); 3.09-2.92 (m, 4H, —CH$_2$—N—CH$_2$); 1.39 (s, 9H, tert-But).
MS, m/e 636.2 (M$^+$), calcd: 635.71
MP.=decomp.

t-But-N,-(2-Phthalimido-aminoethyl),N-(2-hydroxyethyl) glycinate (15)

$^1$H-NMR ($CDCl_3$):
7.84 (m, 2H—Ar); 7.68 (m, 2H—Ar); 3.75 (t, 2H, CH$_2$-(Pht-N); 3.48 (t, 2H, CH$_2$—OH); 3.29 (s, 2H, CH$_2$—COO-tert-But); 2.94-2.2.80 (m, 4H, (CH$_2$) N—(CH$_2$)); 1.39 (s, 9H, tert-But).
MS, m/e 349.1 (M$^+$), calcd: 348.7
MP.=158° C.

| Phtalimide Monomers | Mass Spectra data | |
|---|---|---|
| | calculated MW | Found |
| 16T | 560.6 | 561.1 |
| 16G | 718.29 | 719.2 |
| 16A | 465.21 | 466.2 |
| 16C | 636.2 | 635.7 |
| 15 | 348.7 | 349.1 |

Peptide Nucleic Acid Analogs (PNA Oligomers) Comprising Positively Charged PNA

An oligomeric PNA utilizing the "flag approach" was synthesized incorporating a stretch of positively charged PNA analogs of the present invention. On the left of the sequence in bold (from C to C) is the sequence fraction built from the positively charged PNA of the invention. The NH2 moiety is the terminal end of the sequence. The other part of the sequence (G to T, starting with COOH) was built from standard (regular) PNAs. The assembly of the PNA on the resin starts from the amino acid Lysine. The resin is Wong resin and the method used in this example was the Fmoc method.

H2NCCTCCCTCCCGGAG-Lys-COOH (SEQ ID NO: 1)

All procedures were carried by coupling methods as are well known to the skilled artisan.

Examples of Possible Antisense Candidates:

| Diseases | Target | Reference |
|---|---|---|
| 1. Stroke | Inducible Nitric Oxide | Ref. 32 |
| 2. Stroke | Tumor Necrosis Factor-α | Ref. 33 |
| 3. Stroke | NMDA-Ri | Ref. 34 |
| 4. Stroke | Intracellular adhesion molecule-1 (ICAM-1) | Ref. 35 |
| 5. Stroke | p53 | Ref. 36 |
| 6. Stroke | Interleukin-1beta (IL-Ibeta) | Ref. 37 |
| 7. Stroke | Nogo A | Ref. 38 |
| 8. Alzheimer's disease | Beta-secretase | Ref. 39 |
| 9. Alzheimer's disease | acetylcholinesterase (AchE) | Ref. 40 |

-continued

| Diseases | Target | Reference |
|---|---|---|
| 10. Parkinson's disease | Alpha-synuclein | Ref. 41 |
| 11. Parkinson's disease | Dopamine transporter | Ref. 42 |
| 12. Pain | Tetrodotoxin-resistant Na+ channel | Ref. 43 |

The foregoing examples are non-limitative in nature and intended merely to illustrate the principles of the invention. It will be appreciated by the skilled artisan that many variations, modifications and adaptation of these specific embodiments are possible without departing from the scope of the invention, which is defined in the claims that follow.

REFERENCES

1. Stein, C. A., Cohen, J. (1988). Oligodeoxynucleotides as inhibitors of gene expression: a review. Cancer Res. 48:2659-2668.
2. Kiely, J. S., (1994). Recent Advances in Antisense Technology. Annual Reports in Medicinal Chemistry, 29, Academic Press, 30:297-305.
3. Agrawal, S., et al., (1989). Phosphoramidate, phosphorothioate, and methylphosphonate analogs of oligonucleotide: Inhibitors of replication of human immunodeficiency virus. Nucleosides Nucleotides 8:819.
4. Loschner, T., Engels, J. (1988). Methyl phosphoramidites preparation and application in oligodeoxynucleoside methylphosphonate synthesis. Nucleosides Nucleotides, 7:729-736.
5. Ghosh, M. K., et al., (1993). Evaluation of some properties of phosphorodithioate oligodeoxyribonucleotides for antisense application. Nucleic acids Res, 21: 5761-5766.
6. Weinfeld, M., Livingston, D. C. (1986). Synthesis and properties of oligodeoxyribonucleotides containing an ethylated internucleotide phosphate. Biochemistry 25:5083-5091.
7. Summers, M. F., et al., (1986). Alkyl Phosphotriester modified oligodeoxyribonucleotides. Nucleic Acids Res, 14: 7421-7437.
8. Nielsen, P. E., et al., (1993) Nucleic Acids Res. 21: 197-200.
9. E. Uhlmann., et al., (1998), PNA: Synthetic polyamide nucleic acids with unusual binding properties; Angew. Chem. Int. Ed, 37, 2796-2823.
10. M. Kwahara, et al., (1999), Synthesis of Delta-Amino acids with an ether linkage in the main chain and nucleobases on the side chain as monomer units for oxy-peptide nucleic acids, Tetrahedron, 55: 10067-10078.
11. G. Lowe, T. Vilaivan, (1997), Amino acids bearing nucleobases for the synthesis of novel peptide nucleic acids., J. Chem. Soc. Perkin Trans 1, 539-546; ibid. 547-554; ibid. 555-560.
12. P. Lagriffoule, et al., (1997), Peptide nucleic acids with a conformationally constrained chiral cyclohexyl derived backbone, Chem Eur. J. 3:912-919.
13. B. Hyrup, et al., (1996), A flexible and positively charged PNA analogue with an ethylene-linker to the nucleobase: Synthesis and hybridization properties. Bioorg. Med. Chem. Lett. 6: 1083-1088.
14. B. Falkiewicz, (1999), Peptide nucleic acids and their structural modifications. Acta. Biochim. Pol. 3: 509-529.
15. Brightman, M. W. (1977) Morphology of blood-brain interfaces. Exp. Eye Res 25: 1-25.
16. Oldendorf, W. H. (1974) Lipid solubility and drug penetration of the blood-brain barrier. Proc. Soc. Exp. Biol. Med. 147: 813-816.
17. Temsamani J et al., Brain drug delivery technologies: novel approaches for transporting therapeutics. PSIT Vol. 3, 2000.
18. Grelg N. H. (1989) Drug delivery to the brain by blood-barrier: circumvention and drug modification. In Implications of the Blood-Brain Barrier and its manipulation (Vol. 1) Neuwelt, E. A., ed.), pp. 311-367, Plenum Press, New York, USA.
19. Rousselle, C et al., New advances in the transport of doxorubicin through the blood-brain barrier by a peptide vector-mediated strategy. Mol. Pharmacol. 57, 679-686.
20. Schwarze S R et al (1999) In vivo protein transduction: delivery of a biologically active protein into the mouse. Science 285 1569-1572.
21. Boado and Pardridge (1994) Complete inactivation of target mRNA by biotinylated antisense oligodeoxynucleotide-avidin conjugates. Bioconjug. Chem. 5: 406-410.
22. Wu et al., (1996) Pharmacokinetics of blood-brain barrier transport of [$^3$H]-biotinylated phosphorothioate oligodeoxynucleotide conjugated to a vector-mediated drug delivery system. J. Pharmacol. Exp. Ther. 276 206-211.
23. Pardridge W M. Et al., (1995) Vector mediated delivery of a peptide nucleic acid through the blood-brain barrier in vivo, Proc. Natl. Acad. Sci. USA 92: 5592-5596.
24. Whitesell, L., Geselowitz D., Chavany C., Falmy, B., Walbridge, S., Alger J., Neckers, L. M. Stability, clearance, and disposition of intraventiculary administrated oligodeoxynucleotides: implications for therapeutic application within the central nervous system. Proc. Natl. Acad. Sci. U.S.A. 1993, 90, 4665-4669.
25. Agrawal S., Antisense oligonucleotides: a possible approach for chemotherapy of AIDS. In: Prospects for Antisense Nucleic Acid Therapy of Cancer and AIDS; Wickstrom, E Ed; Wiley-Liss: New York, 1991; pp 143-158.
26. Boado R. J. Antisense drug delivery through the blood-brain barrier. Adv. Drug. Del. Rev. 1995, 15, 73-107.
27. Bickel U., Antibody delivery through the blood-brain barrier. Advanced Drug Delivery Reviews 1995, 15, 53-72.
28. Tsuji A., Tamai I., Carrier-mediated or specialized transport of drugs across the blood-brain barrier. Advanced Drug Delivery Reviews 1999, 36, 277-290.
29. Tamai I et al., Structure-internalization relationship for adsorptive-mediated endocytosis of basic peptides at the blood-brain barrier. JPET, 1997 280, 410-415.
30. Tamai I., Tsuji A., Transporter-mediated permeation of drugs across the blood-brain barrier. J. Pharmac. Sci. 2000, 89, 1371-1388.
31. Bickel U., Yoshikawa T., Pardridge W N. Delivery of peptides and proteins through the blood-brain barrier. Advanced Drug Delivery Reviews 2001, 46, 247-279.
32. Antisense Oligodeoxynucleotide to Inducible Nitric Oxide Synthase Protects Against Transient Focal Cerebral Ischemia-Induced Brain Injury. J. Cere. Blood. Flow. 21: 15-21, 2001.

33. Antisense Oligodeoxynucleotide Inhibition of tumor necrosis factor-Expression is neuroprotective after intracerebral hemorrhage. Stroke. 2001, 32: 240-248.
34. Antisense oligodeoxynucleotides to NMDA-R1 receptor channel protect cortical neurons from excitotoxicity and reduce focal ischaemic infarctions. Nature, 1993, 363 (6426) 260-3.
35. Inhibition of TNF alpha attenuates infarct volume and ICAM-1 expression in ischemic mouse brain. Neuroreport 1998 9 (9) 2131-2134. Antisense oligonucleotide for ICAM-1 attenuate reperfusion injury and renal failure in the rat. Kidney Int 1996 50 (2) 473-480.
36. P53-immunoreactive protein and p53 mRNA expression after transient middle cerebral artery occlusion in rats. Stroke 1994 25(4): 849-855.
37. Inhibition of interleukin-1beta converting enzyme family proteases reduces ischemic and excitotoxic neuronal damage. Proc Natl Acad Sci USA Mar. 4, 1997; 94(5):2007-12.
38. Huber A B, Schwab M E, Nogo A, A potent inhibitor of neurite outgrowth and regeneration. J. Biol. Chem. 2000 May-June; 381(5-6):407-19.
39. Bennett et al., Beta-secretase cleavage of Alzheimer's amyloid precursor protein by the transmembrane aspartic protease BACE., Amgen, Inc., One Amgen Center Drive, M/S 29-2-B, Thousand Oaks, Calif. 91320-1799, USA.
40. Shohami et al., (2000) Antisense prevention of neuronal damages following head injury in mice J Mol Med.; 78(4): 228-36.
41. Duda et al., (2000) Neuropathology of synuclein aggregates. J Neurosci Res. 15; 61(2):121-7.
42. Simantov et al., (1996) Dopamine-Induced apoptosis in human neuronal cells: inhibition by nucleic acids antisense to have dopamine transporter. Neuroscience vol. 74 no. 1 pp. 39-50.
43. Gold M S (1999) Tetrodotoxin-resistant Na$^+$ currents and inflammatory hyperalgesia. PNAS. 1999 60. 7645-7649.
44. Pooga et al., (2001), PNA oligomers as tools for specific modulation of gene expression. Biomolecular Engineering 17: 183-192.
45. Wattiaux et al., (2000) Endosomes, lysosomes: their implication in gene transfer. Adv. Drug. Del. Rev. 41: 201-208.

The invention claimed is:

1. A compound of the general formula (I)

wherein, R1 is hydrogen or a protecting group suitable for protecting an amino group; R2 is hydrogen or a protecting group suitable for the protection of a carboxyl group; and Bn is a protected or unprotected, natural or non-natural nucleobase other than thymine.

2. The compound of claim 1 wherein R1 is hydrogen or a protecting group selected from the group consisting of Monomethoxytrityl (MMT), Dimethoxytrityl (DMTr), Fluorenyloxycarbonyl (Fmoc), tert-Butyloxycarbonyl (t-BOC), Phthalimide (Pht), and Tetrachlorophthalimide (TPht); and R2 is hydrogen or a protecting group selected from the group consisting of Methyl (Me), Ethyl (Et), Propyl (Prop), tert-Butyl (t-Bu), Benzyl (Bnz), and Monomethoxytrityl (MMT).

3. The compound of claim 1 wherein Bn is selected from the group consisting of guanine or protected guanine; pseudoguanine or protected pseudo-guanine (2,6-diaminopurine); adenine or protected adenine; cytosine or protected cytosine; pseudo-cytosine or protected pseudo-cytosine, pseudo-isocytosine or protected pseudo-isocytosine; uracil or protected uracil.

4. The compound of claim 3 wherein Bn is guanine, protected guanine, pseudoguanine or protected pseudoguanine.

5. The compound of claim 4 wherein the protecting group for an amino group of the guanine is selected from the group consisting of i-Butyryl (iBu), acetyl (Ac), and benzoyl (Bz) and the protecting group for the hydroxyl group of the guanine is selected from the group consisting of diphenylcarbamoyl (DPC), and Benzyl (Bnz).

6. The compound of claim 3 wherein Bn is adenine or protected adenine.

SEQUENCE LISTING

<160> NUMBER OF SEQ ID NOS: 1

<210> SEQ ID NO 1
<211> LENGTH: 15
<212> TYPE: DNA
<213> ORGANISM: Artificial Sequence
<220> FEATURE:
<223> OTHER INFORMATION: Chemically Synthesized oligomer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (15)..(15)
<223> OTHER INFORMATION: Lys

<400> SEQUENCE: 1
ncctccctcc cggag                    15

7. The compound of claim 6 wherein the protecting group for the adenine is selected from Benzoyl (Bz), Acetyl (Ac), and Diphenylacetyl (DPA).

8. The compound of claim 3 wherein Bn is cytosine, protected cytosine, pseudo-cytosine, protected pseudo-cytosine, pseudo-isocytosine, or protected pseudo-isocytosine.

9. The compound of claim 8 wherein the protecting group for the cytosine, pseudo-cytosine or pseudo-isocytosine is selected from the group consisting of Benzoyl (Bz), Acetyl (Ac), and Diphenylacetyl (DPA).

10. The compound of claim 3 wherein Bn is uracil or protected uracil.

11. The compound of claim 10 wherein the protecting group for the uracil is selected from Benzoyl (Bz), Acetyl (Ac), and Diphenylacetyl (DPA).

12. An oligomer comprising at least one peptide nucleic acid analog IP-PNA of the general formula (I)

wherein, R1 is hydrogen or a protecting group suitable for protecting an amino group; R2 is hydrogen or a protecting group suitable for the protection of a carboxyl group; and Bn is a protected or unprotected, natural or non-natural nucleobase other than thymine.

13. The oligomer of claim 12 wherein the oligomer is conjugated to polyethyleneglycol.

14. The oligomer of claim 12 wherein from about 5 to 10 IP-PNA monomers are incorporated at one or both termini into oligomers comprising from about 10 to 30 ordinary PNA units.

15. The oligomer of claim 14, comprising the sequence: A-A-A(n)-A-A-IP-PNA-IP-PNA-IP-PNA-X wherein A is a polyamide nucleic acid monomer; n is a number from about 5 to 25; IP-PNA is a compound of the general formula (I) from which all protecting groups have been removed and R1 and R2 have been replaced by covalent bonds between adjacent monomers; and X is selected from the group consisting of a free carboxylic acid, a reduced carboxylic group, and polyethyleneglycol.

16. The oligomer of claim 12 comprising IP-PNA units incorporated into a sequence of from about 10 to about 30 nucleobases.

17. The oligomer of claim 16 comprising the sequence: IP-PNA-TP-PNA-IP-PNA(m)-IP-PNA-X, wherein m is a number from about 6 to 26; IP-PNA is a compound of the general formula (I) from which all protecting groups have been removed and R1 and R2 have been replaced by covalent bonds between adjacent monomers; and X is selected from the group consisting of a free carboxylic acid, a reduced carboxylic group, and polyethyleneglycol.

18. The oligomer of claim 12 comprising alternating units of IP-PNA monomers and PNA monomers.

19. The oligomer of claim 18 comprising the sequence: A-IP-PNA-A-IP-PNA-(A-IP-PNA)m-A-IP-PNA-X, wherein A is a polyamide nucleic acid monomer; m is a number from about 5 to 25; IP-PNA is a compound of the general formula (I) from which all protecting groups have been removed and R1 and R2 have been replaced by covalent bonds between adjacent monomers; and X is selected from the group consisting of a free carboxylic acid, a reduced carboxylic group, and polyethyleneglycol.

20. A pharmaceutical composition comprising as an active ingredient a compound of the general formula (I):

wherein, R1 is hydrogen or a protecting group suitable for protecting an amino group; R2 is hydrogen or a protecting group suitable for the protection of a carboxyl group; Bn is a protected or unprotected, natural or non-natural nucleobase; and further comprising any pharmaceutically acceptable diluent or vehicle.

21. A pharmaceutical composition comprising as an active ingredient the oligomer of claim 12, further comprising any pharmaceutically acceptable diluent or vehicle.

22. A pharmaceutical composition comprising as an active ingredient the oligomer of claim 12 comprising a plurality of IP-PNA units, further comprising any pharmaceutically acceptable diluent or vehicle.

23. The pharmaceutical composition of claim 21 for targeting antisense molecules to a central nervous system.

24. The pharmaceutical composition of claim 22 for targeting antisense molecules to a central nervous system.

* * * * *